US012624078B2

(12) United States Patent
Zhao et al.

(10) Patent No.: US 12,624,078 B2
(45) Date of Patent: May 12, 2026

(54) MODIFIED INTERLEUKIN-2 (IL-2) MOLECULE AND USE THEREOF

(71) Applicant: LETO LABORATORIES CO., LTD, Beijing (CN)

(72) Inventors: Yao Zhao, Beijing (CN); Yu Zhang, Beijing (CN); Huijie Liu, Beijing (CN); Jinhua Piao, Beijing (CN); Jianjun Zhang, Beijing (CN); Qiulei Zhang, Beijing (CN); Wei Zhang, Beijing (CN); Guoyong Wang, Beijing (CN); Tianfu Zhang, Beijing (CN)

(73) Assignee: LETO LABORATORIES CO., LTD, Beijing (CN)

( * ) Notice: Subject to any disclaimer, the term of this patent is extended or adjusted under 35 U.S.C. 154(b) by 547 days.

(21) Appl. No.: 18/029,673

(22) PCT Filed: Oct. 16, 2021

(86) PCT No.: PCT/CN2021/124246
§ 371 (c)(1),
(2) Date: Mar. 31, 2023

(87) PCT Pub. No.: WO2022/078518
PCT Pub. Date: Apr. 21, 2022

(65) Prior Publication Data
US 2023/0416326 A1     Dec. 28, 2023

(30) Foreign Application Priority Data

Oct. 18, 2020    (CN) ........................... 202011113975.7
Oct. 15, 2021    (CN) ........................... 202111201233.4

(51) Int. Cl.
*C07K 14/55*     (2006.01)
*A61P 35/00*     (2006.01)
*C07K 14/54*     (2006.01)
*C07K 14/715*     (2006.01)
*A61K 38/00*     (2006.01)

(52) U.S. Cl.
CPC .............. *C07K 14/55* (2013.01); *A61P 35/00* (2018.01); *C07K 14/5443* (2013.01); *C07K 14/7155* (2013.01); *A61K 38/00* (2013.01); *C07K 2319/30* (2013.01)

(58) Field of Classification Search
CPC .................................................... C07K 14/55
See application file for complete search history.

(56) References Cited

U.S. PATENT DOCUMENTS

| | | |
|---|---|---|
| 7,858,081 B2 | 12/2010 | Bernard et al. |
| 2007/0160578 A1 | 7/2007 | Waldmann et al. |
| 2020/0002398 A1 | 1/2020 | Silva Manzano et al. |

FOREIGN PATENT DOCUMENTS

| | | |
|---|---|---|
| AU | 2012215572 A1 | 5/2013 |
| CA | 3098765 A1 | 3/2020 |
| CN | 105440123 A | 3/2016 |
| CN | 110437339 A | 11/2019 |
| CN | 111018961 A | 4/2020 |
| CN | 111647068 A | 9/2020 |
| EA | 033369 B1 | 10/2019 |
| RU | 2013139267 A | 3/2015 |
| WO | 2019213517 A1 | 11/2019 |
| WO | 2020125743 A1 | 6/2020 |
| WO | 2021185361 A1 | 9/2021 |

OTHER PUBLICATIONS

Bernard, Jérôme et al., "Identification of an interleukin-15alpha receptor-binding site on human interleukin-15", Journal of Biological Chemistry, vol. 279, No. 23, Jun. 4, 2004, pp. 24313-24322.
J. Fernando Bazan, Unraveling the Structure of IL-2, Science, 1992, pp. 410-412, vol. 257, No. 5068.
Yasuhiro Minami, et al., The IL-2 Receptor Complex: Its Structure, Function, and Target Genes, Annu. Rev. Immunol., 1993, pp. 245-268, vol. 11.
David C. Lowe, et al., Engineering a High-Affinity Anti-IL-15 Antibody: Crystal Structure Reveals an α-Helix in VH CDR3 as Key Component of Paratope, Journal of Molecular Biology, 2011, pp. 160-175, vol. 406.
Thomas A. Waldmann, et al., The biology of interleukin-2 and interleukin-15: implications for cancer therapy and vaccine design, Nature Reviews Immunology, 2006, pp. 595-601, vol. 6.
J. Sambrook, et al., Molecular Cloning: A Laboratory Manual, 1989, Second Edition, Cold Spring Harbor Laboratory Press.
Yunier Rodriguez-Alvarez, et al., Obtention and characterization of the recombinant simian Interleukin-15 in *Escherichia coli* for the preclinical assessment of an IL-15-based therapeutic vaccine, Preparative Biochemistry and Biotechnology, 2017, pp. 889-900, vol. 47, No. 9.
Patricia Estep, et al., High throughput solution-based measurement of antibody-antigen affinity and epitope binning. MAbs, 2013, pp. 270-278, vol. 5, Issue 2.

(Continued)

*Primary Examiner* — Prema M Mertz
(74) *Attorney, Agent, or Firm* — NKL Law; Allen Xue

(57) ABSTRACT

A modified interleukin-2 (IL-2) molecule is obtained by being subjected to a modification as follows: substituting a region in an IL-2 molecule that mediates the binding of the IL-2 molecule to interleukin-2 receptor alpha (IL2Rα) with a region in an interleukin-15 (IL-15) molecule that mediates the binding of the IL-15 molecule to interleukin-15 receptor alpha (IL15Rα). The region in the IL-15 molecule that mediates the binding of the IL-15 molecule to the IL15Rα includes 9 or more amino acid residues. Furthermore, a protein heterodimer including the modified IL-2 molecule and IL15Rα (a Sushi domain) or a variant thereof is provided. The modified IL-2 molecule and/or the protein heterodimer including the modified IL-2 significantly reduce(s) an affinity of IL2Rα to greatly reduce its side effects in clinical treatment and is promising drug candidate.

2 Claims, 7 Drawing Sheets

Specification includes a Sequence Listing.

(56)     References Cited

OTHER PUBLICATIONS

Kai-Ping Han, et al., IL-15:IL-15 receptor alpha superagonist complex: High-level co-expression in recombinant mammalian cells, purification and characterization, Cytokine, 2011, pp. 804-810, vol. 56.

QIAprep® Spin Miniprep Kit, Sample & Assay Technologies, 2010.

Endo Free® Plasmid Maxi Kit, Sample to Insight, 2016.

Chapter 5, Gel Electrophoresis of DNA and Pulsed-field Agarose Gel Electrophoresis, pp. 5.2-5.89.

Chapter 16, Introducing Cloned Genes into Cultured Mammalian Cells, pp. 16.1-16.62.

| | Positive control IL-2 | Complex 1 |
|---|---|---|
| EC50 nM | 0.07011 | 0.03469 |

FIG. 3

Tumor growth curve

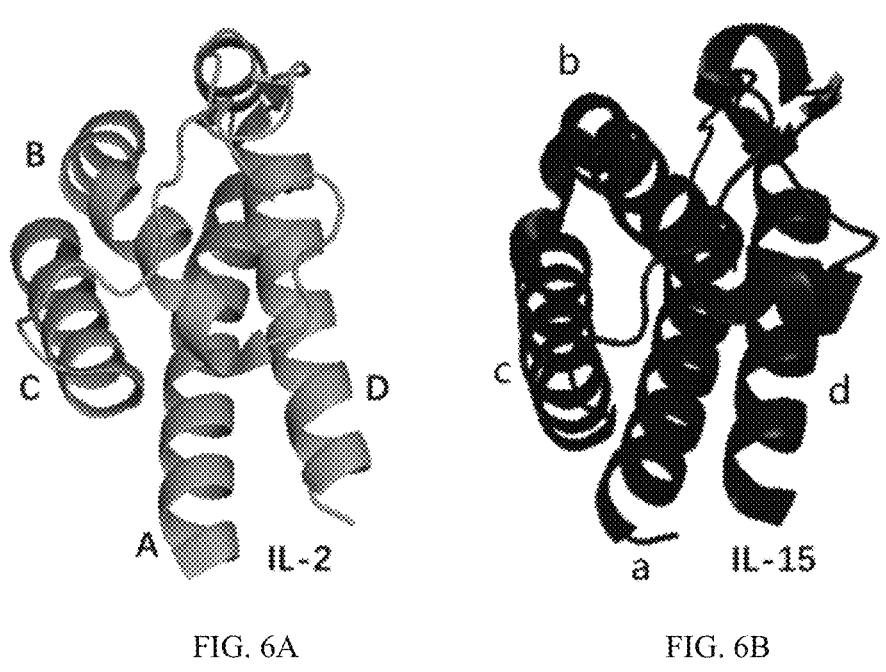
FIG. 6A                                                              FIG. 6B
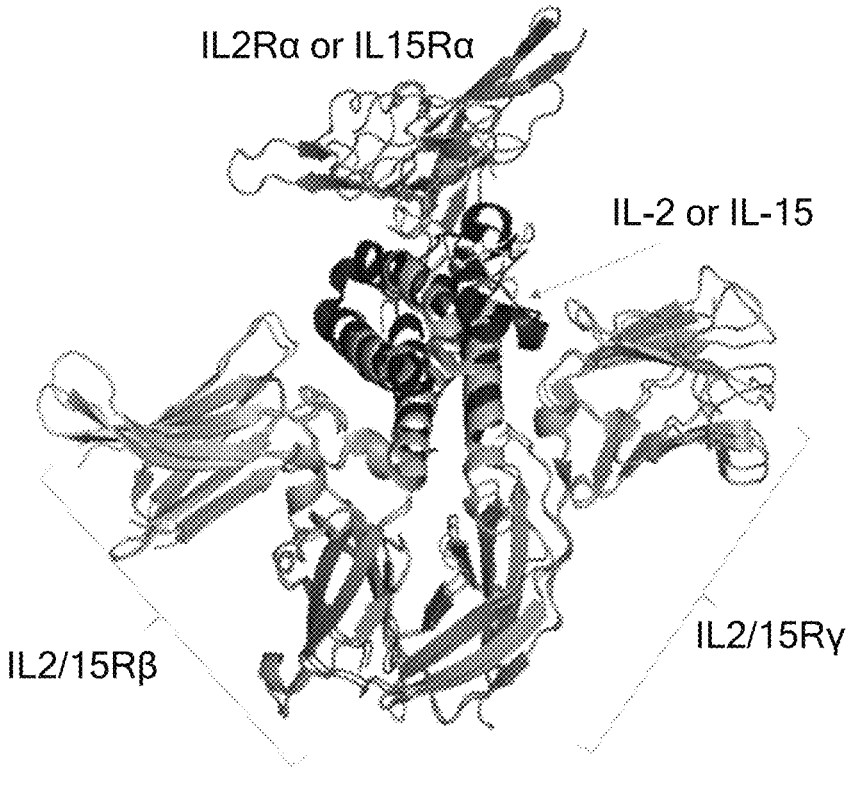
FIG. 7

1

MODIFIED INTERLEUKIN-2 (IL-2) MOLECULE AND USE THEREOF

CROSS REFERENCE TO THE RELATED APPLICATIONS

This application is the national phase entry of International Application No. PCT/CN2021/124246, filed on Oct. 16, 2021, which is based upon and claims priority to Chinese Patent Application No. 202011113975.7, filed on Oct. 18, 2020, and Chinese Patent Application No. 202111201233.4, filed on Oct. 15, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHJL009_Sequence Listing.txt, created on 02/21/2023, and is 27,031 bytes in size.

TECHNICAL FIELD

The present application belongs to the field of biomedicine, and in particular, to a modified interleukin-2 (IL-2) molecule and a use thereof.

BACKGROUND

According to data released by the World Health Organization (WHO) in February 2017, there are more than 14 million new cancer cases worldwide every year, and this number is expected to increase to more than 21 million by 2030; and 8.8 million people die of cancer every year, and global cancer deaths account for nearly one-sixth of the total deaths. The prevention and treatment of cancer is a worldwide problem that needs to be solved urgently in the medical field.

Currently, traditional methods for treating cancer include surgery, chemotherapy, hormone therapy, and radiotherapy (see, for example, Stockdale, 1998, *Principles of Cancer Patient Management*; and *Scientific American: Medicine*, Volume 3, edited by Rubenstein and Federman, Chapter 12, Section IV). However, surgery may be infeasible due to the patient's health or the disease being too advanced, and cancer cells often cannot be completely removed from the body of a patient after surgery. Radiotherapy is effective only when a tumor tissue is more susceptible to radiation than a normal tissue, and high-dose radiation often causes severe side effects. Hormone therapy is rarely used alone, and while the hormone therapy may be effective, it is often used to prevent or delay cancer recurrence after most of cancer cells are removed by other treatments. The biggest problem with chemotherapy is that a patient may quickly develop resistance to a chemotherapeutic agent.

In addition, immunomodulatory factors (such as interleukins (ILs)) can also exert an antitumor effect in animal models and cancer patients, and the use of immunomodulatory factors can avoid the above-mentioned deficiencies in conventional therapies. However, systemic toxic side effects associated with immunomodulatory factors largely limit their use. Therefore, it is necessary to develop an effective therapy that can reduce the toxic side effects of immunomodulatory factors.

SUMMARY

In view of the above problems in the prior art, in a first aspect, the present application provides a modified IL-2 molecule. The modification includes substituting a region in an IL-2 molecule that mediates the binding of the IL-2 molecule to interleukin-2 receptor alpha (IL2Rα) with a region in an interleukin-15 (IL-15) molecule that mediates the binding of the IL-15 molecule to interleukin-15 receptor alpha (IL15Rα). The region in the IL-15 molecule that mediates the binding of the IL-15 molecule to the IL15Rα includes 9 or more amino acid residues.

In some embodiments, the region in the IL-15 molecule that mediates the binding of the IL-15 molecule to the IL15Rα may be a contiguous amino acid sequence.

In some embodiments, the region in the IL-15 molecule that mediates the binding of the IL-15 molecule to the IL15Rα may be a noncontiguous amino acid sequence.

In some embodiments, the region in the IL-15 molecule that mediates the binding of the IL-15 molecule to the IL15Rα may include one or more noncontiguous amino acid sites.

In some embodiments, the region in the IL-2 molecule that mediates the binding of the IL-2 molecule to the IL2Rα may be a contiguous amino acid sequence.

In some embodiments, the region in the IL-2 molecule that mediates the binding of the IL-2 molecule to the IL2Rα may be a noncontiguous amino acid sequence.

In some embodiments, the region in the IL-2 molecule that mediates the binding of the IL-2 molecule to the IL2Rα may include one or more noncontiguous amino acid sites.

In some embodiments, the modification can reduce an affinity of the modified IL-2 molecule for the IL2Rα.

In some embodiments, the modification can eliminate the affinity of the modified IL-2 molecule for the IL2Rα.

In some embodiments, the affinity may be measured by a biolayer interferometry (BLI).

In some embodiments, the region in the IL-2 molecule that mediates the binding of the IL-2 molecule to the IL2Rα may include a loop M or a variant thereof, and the loop M may include a sequence shown in SEQ ID NO: 1.

In some embodiments, the region in the IL-2 molecule that mediates the binding of the IL-2 molecule to the IL2Rα may include a loop N or a variant thereof, and the loop N may include a sequence shown in SEQ ID NO: 5.

In some embodiments, the region in the IL-2 molecule that mediates the binding of the IL-2 molecule to the IL2Rα may include a helix B or a variant thereof, and the helix B may include a sequence as shown in SEQ ID NO: 2.

In some embodiments, the region in the IL-2 molecule that mediates the binding of the IL-2 molecule to the IL2Rα may include a loop M or a variant thereof and a helix B or a variant thereof; and the loop M may include a sequence as shown in SEQ ID NO: 1, and the helix B may include a sequence shown in SEQ ID NO: 2.

In some embodiments, the region in the IL-2 molecule that mediates the binding of the IL-2 molecule to the IL2Rα may include a helix B or a variant thereof and a loop N or a variant thereof; and the helix B may include a sequence shown in SEQ ID NO: 2, and the loop N may include a sequence as shown in SEQ ID NO: 5.

In some embodiments, the region in the IL-2 molecule that mediates the binding of the IL-2 molecule to the IL2Rα may include a loop M or a variant thereof and a loop N or a variant thereof; and the loop M may include a sequence as shown in SEQ ID NO: 1, and the loop N may include a sequence as shown in SEQ ID NO: 5.

In some embodiments, the region in the IL-2 molecule that mediates the binding of the IL-2 molecule to the IL2Rα may include a loop M or a variant thereof, a helix B or a variant thereof, and a loop N or a variant thereof sequentially from N-terminus to C-terminus; and the loop M may include a sequence as shown in SEQ ID NO: 1, the helix B may include a sequence as shown in SEQ ID NO: 2, and the loop N may include a sequence as shown in SEQ ID NO: 5.

In some embodiments, the region in the IL-15 molecule that mediates the binding of the IL-15 molecule to the IL15Rα may include a loop m or a variant thereof, and the loop m may include a sequence as shown in SEQ ID NO: 8.

In some embodiments, the region in the IL-15 molecule that mediates the binding of the IL-15 molecule to the IL15Rα may include a loop n or a variant thereof, and the loop n may include a sequence as shown in SEQ ID NO: 12.

In some embodiments, the region in the IL-15 molecule that mediates the binding of the IL-15 molecule to the IL15Rα may include a helix b or a variant thereof, and the helix b may include a sequence as shown in SEQ ID NO: 9.

In some embodiments, the region in the IL-15 molecule that mediates the binding of the IL-15 molecule to the IL15Rα may include a loop m or a variant thereof and a helix b or a variant thereof; and the loop m may include a sequence as shown in SEQ ID NO: 8, and the helix b may include a sequence as shown in SEQ ID NO: 9.

In some embodiments, the region in the IL-15 molecule that mediates the binding of the IL-15 molecule to the IL15Rα may include a helix b or a variant thereof and a loop n or a variant thereof; and the helix b may include a sequence as shown in SEQ ID NO: 9, and the loop n may include a sequence as shown in SEQ ID NO: 12.

In some embodiments, the region in the IL-15 molecule that mediates the binding of the IL-15 molecule to the IL15Rα may include a loop m or a variant thereof and a loop n or a variant thereof; and the loop m may include a sequence as shown in SEQ ID NO: 8, and the loop n may include a sequence as shown in SEQ ID NO: 12.

In some embodiments, the region in the IL-15 molecule that mediates the binding of the IL-15 molecule to the IL15Rα may include a loop m or a variant thereof, a helix b or a variant thereof, and a loop n or a variant thereof sequentially from N-terminus to C-terminus; and the loop m may include a sequence as shown in SEQ ID NO: 8, the helix b may include a sequence as shown in SEQ ID NO: 9, and the loop n may include a sequence as shown in SEQ ID NO: 12.

In some embodiments, the modification may include substituting a loop M or a variant thereof in the region that mediates the binding of the IL-2 molecule to the IL2Rα with a loop m or a variant thereof in the region that mediates the binding of the IL-15 molecule to the IL15Rα.

In some embodiments, the modification may include substituting a helix B or a variant thereof in the region that mediates the binding of the IL-2 molecule to the IL2Rα with a helix b or a variant thereof in the region that mediates the binding of the IL-15 molecule to the IL15Rα.

In some embodiments, the modification may include substituting a loop N or a variant thereof in the region that mediates the binding of the IL-2 molecule to the IL2Rα with a loop n or a variant thereof in the region that mediates the binding of the IL-15 molecule to the IL15Rα.

In some embodiments, the modification may include substituting a loop M or a variant thereof in the region that mediates the binding of the IL-2 molecule to the IL2Rα with a loop m or a variant thereof in the region that mediates the binding of the IL-15 molecule to the IL15Rα and substituting a helix B or a variant thereof in the region that mediates the binding of the IL-2 molecule to the IL2Rα with a helix b or a variant thereof in the region that mediates the binding of the IL-15 molecule to the IL15Rα.

In some embodiments, the modification may include substituting a helix B or a variant thereof in the region that mediates the binding of the IL-2 molecule to the IL2Rα with a helix b or a variant thereof in the region that mediates the binding of the IL-15 molecule to the IL15Rα, and substituting a loop N or a variant thereof in the region that mediates the binding of the IL-2 molecule to the IL2Rα with a loop n or a variant thereof in the region that mediates the binding of the IL-15 molecule to the IL15Rα.

In some embodiments, the modification may include substituting a loop M or a variant thereof in the region that mediates the binding of the IL-2 molecule to the IL2Rα with a loop m or a variant thereof in the region that mediates the binding of the IL-15 molecule to the IL15Rα, and substituting a loop N or a variant thereof in the region that mediates the binding of the IL-2 molecule to the IL2Rα with a loop n or a variant thereof in the region that mediates the binding of the IL-15 molecule to the IL15Rα.

In some embodiments, the modification may include substituting a loop M or a variant thereof in the region that mediates the binding of the IL-2 molecule to the IL2Rα with a loop m or a variant thereof in the region that mediates the binding of the IL-15 molecule to the IL15Rα, substituting a helix B or a variant thereof in the region that mediates the binding of the IL-2 molecule to the IL2Rα with a helix b or a variant thereof in the region that mediates the binding of the IL-15 molecule to the IL15Rα, and substituting a loop N or a variant thereof in the region that mediates the binding of the IL-2 molecule to the IL2Rα with a loop n or a variant thereof in the region that mediates the binding of the IL-15 molecule to the IL15Rα.

In some embodiments, the modification may enable the modified IL-2 molecule to bind to the IL15Rα or a Sushi domain of the IL15Rα.

In some embodiments, the modification may further include substituting a loop X or a variant thereof in the IL-2 molecule with a loop x or a variant thereof in the IL-15 molecule; and the loop x may include a sequence as shown in SEQ ID NO: 10, and the loop X may include a sequence as shown in SEQ ID NO: 3.

In some embodiments, the modification may further include substituting a helix C or a variant thereof in the IL-2 molecule with a helix c or a variant thereof in the IL-15 molecule; and the helix c may include a sequence as shown in SEQ ID NO: 11, and the helix C may include a sequence as shown in SEQ ID NO: 4.

In some embodiments, the substitution may make the modified IL-2 molecule have higher stability than an IL-2 molecule without the substitution of the helix c.

In some embodiments, the modification may further include an amino acid substitution in a helix D region of the IL-2 molecule. A substitute amino acid and the 43rd phenylalanine (F) in the helix b form an aromatic ring interaction to stabilize a hydrophobic core. The position of the 43rd phenylalanine (F) is based on the amino acid sequence of a natural IL-15 molecule and is determined according to an EU index numbered by KABAT. The helix D may include a sequence as shown in SEQ ID NO: 6.

In some embodiments, the amino acid sequence of the natural IL-15 molecule may be shown in SEQ ID NO: 13.

In some embodiments, the amino acid substitution may include W121F, where a position of a substitute amino acid is based on an amino acid sequence of a natural IL-2 molecule and is determined according to the EU index numbered by KABAT.

In some embodiments, the amino acid sequence of the natural IL-2 molecule may be shown in SEQ ID NO: 7.

In some embodiments, the modified IL-2 molecule may include a sequence as shown in SEQ ID NO: 14.

In a second aspect, the present application also provides a protein heterodimer, where the protein heterodimer includes the modified IL-2 molecule described in the present application and IL15Rα or a variant thereof; or, the protein heterodimer includes the modified IL-2 molecule described in the present application and a Sushi domain of the IL15Rα or a variant thereof.

In some embodiments, the IL15Rα may include a sequence as shown in SEQ ID NO: 16.

In some embodiments, the Sushi domain may include a sequence as shown in SEQ ID NO: 15 or SEQ ID NO: 20.

In some embodiments, the protein heterodimer may not bind to IL2Rα and may exhibit a higher affinity for interleukin-2 receptor beta (IL2Rβ) than an IL-2 molecule; the IL-2 molecule may include a natural IL-2 molecule and a functional variant thereof.

In some embodiments, the functional variant of the natural IL-2 molecule may include the modified IL-2 molecule.

In some embodiments, the variant of the IL15Rα or the variant of the Sushi domain may include an Fc fragment.

In some embodiments, the Fc fragment may be located at C-terminus of the IL15Rα or the Sushi domain.

In some embodiments, the Fc fragment may include any one selected from the group consisting of human IgG1 Fc, human IgG4 Fc, and mouse IgG2aa.1 Fc fragments.

In some embodiments, the Fc fragment may include a sequence as shown in SEQ ID NO: 18, SEQ ID NO: 24, or SEQ ID NO: 25.

In some embodiments, the protein heterodimer may include a sequence as shown in SEQ ID NO: 14 and a sequence as shown in SEQ ID NO: 19, SEQ ID NO: 21, or SEQ ID NO: 22.

In some embodiments, the modified IL-2 molecule and the protein heterodimer described in the present application can reduce the proliferation activity of regulatory T (Treg) cells compared with unmodified IL-2 molecules.

In a third aspect, the present application also provides a nucleic acid encoding the modified IL-2 molecule described in the present application.

In a fourth aspect, the present application provides a nucleic acid combination encoding a) the modified IL-2 molecule described in the present application and b) the IL15Rα or the variant thereof or the Sushi domain or the variant thereof described in the present application.

In a fifth aspect, the present application also provides a vector carrying the nucleic acid described in the present application or the nucleic acid combination described in the present application.

In some embodiments, a nucleic acid encoding the modified IL-2 molecule described in the present application and a nucleic acid encoding the IL15Rα or the variant thereof or the Sushi domain or the variant thereof described in the present application may be located in the same vector.

In some embodiments, the vector may include a first vector and a second vector, where the first vector carries the nucleic acid encoding the modified IL-2 molecule described in the present application, and the second vector carries the nucleic acid encoding the IL15Rα or the variant thereof or the Sushi domain or the variant thereof described in the present application.

In a sixth aspect, the present application also provides a cell including the modified IL-2 molecule described in the present application, the protein heterodimer described in the present application, the nucleic acid described in the present application, the nucleic acid combination described in the present application, or the vector described in the present application.

In a seventh aspect, the present application also provides a pharmaceutical composition including the modified IL-2 molecule described in the present application, the protein heterodimer described in the present application, the nucleic acid described in the present application, the nucleic acid combination described in the present application, the vector described in the present application, or the cell described in the present application.

In an eighth aspect, the present application also provides a use of the modified IL-2 molecule described in the present application, the protein heterodimer described in the present application, the nucleic acid described in the present application, the nucleic acid combination described in the present application, the vector described in the present application, or the cell described in the present application in the preparation of a drug for preventing and/or treating a tumor.

In some embodiments, the tumor may include anal cancer, biliary tract cancer, bladder cancer, breast cancer, cervical cancer, gastric cancer, colon cancer, head and neck squamous cell carcinoma (HNSCC), liver cancer, solid tumor, melanoma, Merkel cell carcinoma, mesothelioma, non-small cell lung cancer (NSCLC), ovarian cancer, renal cell carcinoma (RCC), cutaneous squamous cell carcinoma (cSCC), small cell lung cancer (SCLC), thymic carcinoma, thyroid cancer, colon cancer, and/or melanoma.

Clinically, IL-2 at a low dose will preferentially bind to a high-affinity receptor with a chain a on a surface of Treg cells, which results in immunosuppression, such that a therapeutic effect cannot be achieved. IL-2 at a high dose can neutralize the immunosuppression caused by Treg activation by activating a large number of effector T cells, which will also cause many toxic side effects and activation-induced cell death (AICD). By substituting a polypeptide sequence in IL-2 that binds to IL2Rα with a polypeptide sequence in IL-15 that binds to IL15Rα, the binding to the receptor α is weakened or eliminated to reduce the IL-2-promoted anti-T cell proliferation activity and the binding to the endothelial cell receptor α is reduced to reduce or eliminate the toxic side effects caused by IL-2 treatment. In view of this advantage, the modified IL-2 molecule provided in the present application has promising clinical application prospects.

BRIEF DESCRIPTION OF THE DRAWINGS

FIG. 1A is for a complex 1, FIG. 1B is for a complex 2, and FIG. 1C is for a complex 3.

FIG. 3 shows the influence of a complex 1 on the proliferation of CTLL-2 (T cells) in Example 4 of the present application.

FIGS. 6A-6B are schematic diagrams of four-helix structures of IL-2 and IL-15, where 4 helices a of IL-2 are respectively named as helices A\B\C\D and 4 helices a of IL-15 are respectively named as helices a\b\c\d.

FIG. 7 is a schematic diagram illustrating the comparison of the structural superposition between complexes of IL-15 and IL-2 with each receptor, where in the middle IL-2 or IL-15 region: gray represents IL-2 and black represents IL-15.

DETAILED DESCRIPTION OF THE EMBODIMENTS

Figure 1A:
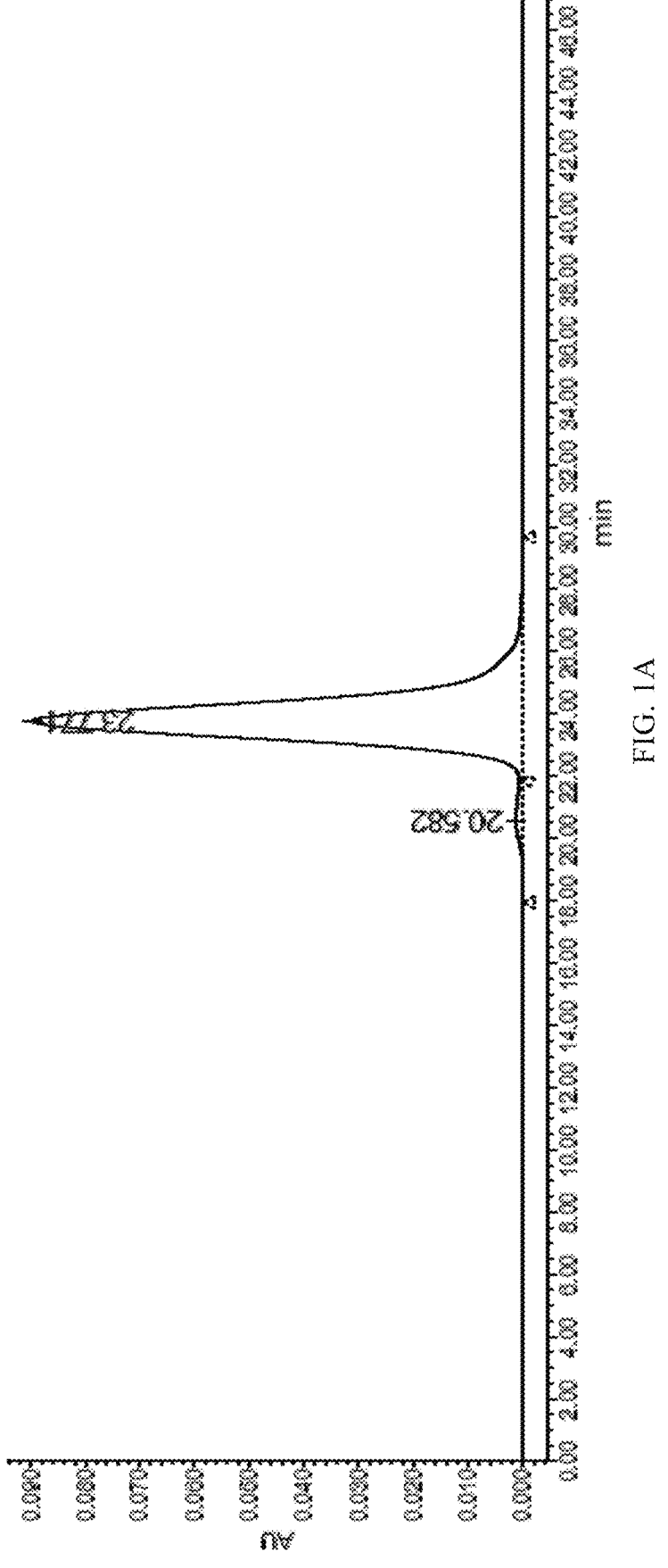
FIGS. 1A-1C show size exclusion chromatography (SEC-HPLC) identification results of a purified heterodimer product of an IL-2/15 chimera 1 and a Sushi-Fc protein in Example 1 of the present application, where

In the present application, the term "IL-2" generally refers to natural IL-2 or a functional variant thereof. Natural IL-2 is a cytokine mainly produced by T cells (which can also be produced by B cells, natural killer (NK) cells, monocytes, and macrophages) and is a globular glycoprotein that plays an important role in maintaining the normal functions of T lymphocytes and NK cells. Natural IL-2 was discovered in 1976 and was then known as T cell growth factor (TCGF). In humans, IL-2 is encoded by a gene on chromosome 4. IL-2 is a polypeptide composed of 133 amino acid residues, which has a molecular weight of about 15 kD and includes three cysteine residues located at positions 58, 105, and 125, respectively. Post-translational modifications (PTMs) of IL-2 include the Thr glycosylation at position 3, the generation of a disulfide bond between cysteine residues at positions 58 and 105, and the generation of a high-level structure mainly composed of 4 helices a and some linking sequences (loops) that is essential for the functions of the IL (Bazan et al., Science 257, 410-413 (1992)). For example, in the present application (as shown in FIGS. 6A-6B), 4 helices a from N-terminus to C-terminus in IL-2 are respectively named as helix A, helix B, helix C, and helix D. A linking sequence (loop) between helices A and B is named as loop M, a linking sequence (loop) between helices B and C is named as loop X, and a linking sequence (loop) between helices C and D is named as loop N. For example, the helix B may include an amino acid sequence as shown in SEQ ID NO: 2, the helix C may include an amino acid sequence as shown in SEQ ID NO: 4, and the helix D may include an amino acid sequence as shown in SEQ ID NO: 6. The loop M may include an amino acid sequence as shown in SEQ ID NO: 1, the loop X may include an amino acid sequence as shown in SEQ ID NO: 3, and the loop N may include an amino acid sequence as shown in SEQ ID NO: 5.

IL-2 mediates an effect of an IL-2 receptor (IL2R) by binding to the IL2R. A natural IL2R is composed of 3 subunits, namely α (CD25), β (CD122), and γ (CD132) receptor subunits (as shown in FIG. 7). The receptor α is mainly expressed on a surface of Treg cells and some endothelial cells, and the receptor subunits β and γ are mostly expressed on effector T cells (Teff) and NK cells. IL-2 shows different affinities for different receptor subunit complex forms, where IL-2 exhibits the highest affinity for a complex composed of receptor subunits α, β, and γ and exhibits a moderate affinity (about 100-fold decrease) for a complex composed of receptor subunits β and γ. IL-2 can signal after binding to each of the two receptor subunit combinations (Minami et al., Annu Rev Immunol 11, 245-268 (1993)).

In the present application, the term "IL-15" generally refers to natural IL-15 or a functional variant thereof. IL-15 is a cytokine that can be produced by various cells, such as activated monocytes and macrophages, epidermal cells, or fibroblasts. A natural human IL-15 mature peptide includes 114 amino acids, has a molecular weight of about 12 kD to 14 kD, is composed of 4 helices a and some linking sequences (loops), and includes 4 cysteine residues, where Cys35 and Cys85 are linked and Cys42 and Cys88 are linked. Disulfide bonds generated in the two pairs of molecules can play an important role in maintaining the spatial conformation and biological activity of IL-15 (Lowe D. C., et al. J. Mol. Biol. 406: 160-175, 2011). For example, in the present application (as shown in FIGS. 6A-6B), 4 helices a from N-terminus to C-terminus in IL-15 are named as helix a, helix b, helix c, and helix d, respectively. A linking sequence (loop) between helices a and b is named as loop m, a linking sequence (loop) between helices b and c is named as loop x, and a linking sequence (loop) between helices c and d is named as loop n. For example, the helix b may include an amino acid sequence as shown in SEQ ID NO: 9, and the helix c may include an amino acid sequence as shown in SEQ ID NO: 11. The loop m may include an amino acid sequence as shown in SEQ ID NO: 8, the loop x may include an amino acid as sequence shown in SEQ ID NO: 10, and the loop n may include an amino acid sequence as shown in SEQ ID NO: 12.

IL-15 can play a role in normal immune responses of the body, such as promoting the development and proliferation of T cells, B cells, and NK cells. IL-15 and IL-2 share the same IL2/15 receptors β and γ but have different receptors α (FIG. 7), such that IL-2 has the functions of Treg cell activation and AICD, while IL-15 of the same family does not have the functions of Treg activation and AICD (Waldmann T A et al, Nature Reviews Immunol 6: 595-601, 2006). In addition, because IL-15 is composed of different receptor subunits, IL-15 exhibits a more significant effect of promoting NK cell proliferation and maintaining memory T cells than IL-2. Therefore, in the present application, based on the characteristics of IL-2 and IL-15, a partial sequence in IL-2 is substituted with a partial sequence in IL-15 to block the binding to IL2Rα and retain the binding to IL2/15Rβ and γ.

In the present application, the term "region that mediates the binding of an IL-15 molecule to IL15Rα" generally refers to a full length or a portion of a sequence in the IL-15 molecule (including a natural IL-15 molecule or a functional variant thereof) that enables the binding of the IL-15 molecule to its receptor subunit α. The region that mediates the binding of the IL-15 molecule to the IL15Rα may be a contiguous amino acid sequence in a polypeptide sequence of the IL-15 molecule or a noncontiguous amino acid sequence therein, such as a combination of several nonadjacent amino acid sites.

In the present application, the term "region that mediates the binding of an IL-2 molecule to IL2Rα" generally refers to a full length or a portion of a sequence in the IL-2 molecule (including a natural IL-2 molecule or a functional variant thereof) that enables the binding of the IL-2 molecule to its receptor subunit α. The region that mediates the binding of the IL-2 molecule to the IL2Rα may be a contiguous amino acid sequence in a polypeptide sequence of the IL-2 molecule or a noncontiguous amino acid sequence therein, such as a combination of several nonadjacent amino acid sites.

In the present application, the term "BLI" generally refers to an experimental technique widely used in kinetic experiments and quantitative detection experiments between biomolecules. For example, BLI can detect an interaction between biomolecules in real time, and thus is widely used in the determination of kinetic constants of proteins, nucleic acids, and other biomolecules. For example, BLI can provide kinetic information including the association rate constant (Ka), dissociation rate constant (Kd), and affinity constant (KD). For example, a principle of BLI may be as follows: A biomolecule A binds to an end of a biosensor (such as an optical fiber material) to form a biofilm. When the molecule A at the end of the biosensor binds to a molecule B to be tested, a molecular weight of the end of the biosensor will change, which will lead to a change in thickness of the biofilm. After light passes through the biofilm of the biosensor, an interference light wave is formed due to transmission and reflection, and the change in thickness of the biofilm causes a relative displacement of the interference light wave. The interference light waves before and after the binding of the biomolecules are detected by a spectrometer to form an interference spectrum, which is displayed by the real-time displacement (nm) of the interference spectrum. Finally, the molecule to be tested is analyzed according to the spectral change before and after the binding of the molecules.

In the present application, the term "natural" generally refers to a substance (such as a protein, a nucleic acid, and another compound molecule) in the nature, which is isolated and identified without artificially changing its structure, such as a natural IL-15 molecule and a natural IL-2 molecule.

In the present application, the term "variant" generally refers to a polypeptide sequence obtained through an amino acid modification (such as group substitution) or the insertion, substitution, and/or deletion of one or more amino acids (such as the deletion of a truncated form of an amino acid sequence) based on a natural polypeptide sequence. A variant may or may not retain the functions of the original natural polypeptide sequence in whole or in part and may also have improved functions (for example, increased affinity for a corresponding ligand or receptor) compared with the original natural polypeptide sequence. A variant that retains the functions of the original natural polypeptide sequence in whole or in part or has improved functions compared with the original natural polypeptide sequence can be referred to as a functional variant. For example, the functional variant may exhibit a better biological activity (or function) than the original sequence. For example, the retention is not necessarily a complete retention. For example, the functional variant may substantially retain a function of the original sequence. For example, the functional variant may retain at least 50%, 60%, 65%, 70%, 75%, 80%, 85%, 90%, 95%, 96%, 97%, 98%, or 99% of the function of the original sequence. For example, the functional variant may have 105%, 110%, 115%, 125%, 140%, 160%, 180%, 200%, 230%, or 260% of the function of the original sequence. For example, an amino acid sequence of the functional variant may be at least 70%, 75%, 80%, 85%, 90%, 95%, 96%, 97%, 98%, or 99% identical to the original amino acid sequence.

In the present application, the term "C-terminus" generally refers to one of the two termini of a polypeptide chain, an amino acid residue at the C-terminus carries free α-carboxyl (—COOH).

In the present application, the term "N-terminus" generally refers to one of the two termini of a polypeptide chain, an amino acid residue at the N-terminus carries free α-amino (—NH₂).

In the present application, the term "including sequentially from N-terminus to C-terminus" generally refers to a positional sequence relationship of sequence fragments or elements included. The sequence fragments or elements need not be directly linked.

In the present application, the term "pharmaceutical composition" generally refers to a composition suitable for administration to a patient, such as a human patient. For example, a pharmaceutical composition described in the present application may include the nucleic acid described in the present application, the vector described in the present application and/or the cell described in the present application, and an optionally pharmaceutically acceptable adjuvant.

In addition, the pharmaceutical composition may further include one or more (pharmaceutically effective) carriers, stabilizers, excipients, diluents, solubilizers, surfactants, emulsifiers, and/or preservatives. The acceptable ingredients of the composition are not toxic to a recipient at the recommended dose and concentration. The pharmaceutical composition of the present disclosure includes, but is not limited to, liquid, frozen, and lyophilized compositions.

In the present application, the term "vector" generally refers to a nucleic acid-delivery vehicle into which a polynucleotide encoding a protein can be inserted to allow the expression of the protein. The vector can be transformed, transduced, or transfected into a host cell, such that a genetic material element carried by the vector can be expressed in the host cell. For example, the vector may include a plasmid; a phagemid; a cosmid; an artificial chromosome, such as a yeast artificial chromosome (YAC), a bacterial artificial chromosome (BAC), or a P1-derived artificial chromosome (PAC); a phage, such as a λ phage or an M13 phage; and a viral vector. The vector may include a variety of elements to control the expression, including a promoter sequence, a transcription initiation sequence, an enhancer sequence, a selection element, and a reporter gene. In addition, the vector may also include a replication origin. The carrier may also include, but is not limited to, components assisting in the entry of the vector into a cell, such as a viral particle, a liposome, or a protein coat.

In the present application, the term "prevention" generally refers to the preventive administration of the composition to a healthy patient to prevent the outbreak of the disease and conditions described in the present application. In addition, the term "prevention" refers to the preventive administration of the composition to a patient in a pre-stage of an allergic disease to be treated. The term "prevention" does not require 100% elimination of the possibility of an event. More accurately, the term "prevention" means that the occurrence probability of an event is reduced in the presence of the pharmaceutical composition or method.

In the present application, the term "treatment" generally refers to the application or administration of a therapeutic agent to a patient or the application or administration of a therapeutic agent to a tissue or cell line isolated from a patient, where the patient suffers from a disease, a disease symptom, or a disease predisposition. The application or administration is conducted to treat, cure, alleviate, relieve, alter, remedy, ameliorate, improve, or affect the disease, the disease symptom, or the disease predisposition, which can include improving a disease status, eliminating a lesion, or improving the prognosis.

In the present application, the terms "tumor" and "cancer" generally refer to cells whose proliferation is at least partially out of control during normal growth and/or development. For example, common tumor or cancer cells often have lost contact inhibition and may be invasive and/or have the ability to metastasize.

In some embodiments of the present application, bioinformatics and protein engineering techniques are used to substitute amino acids in an IL-2 molecule that are mainly responsible for the binding to IL2Rα with a corresponding sequence of IL-15. That is, a loop M (SEQ ID NO: 1) between helices A and B, a helix B (SEQ ID NO: 2), and a loop N (SEQ ID NO: 5) between helices C and D in the IL-2 molecule are substituted with a corresponding sequence of IL-15 (namely, a loop m (SEQ ID NO: 8), a helix b (SEQ ID NO: 9), and a loop n (SEQ ID NO: 12)), thereby blocking the binding of IL-2 to IL2Rα. In order to further improve the structural stability of an IL-2/15 chimera (modified IL-2 molecule), a loop X (SEQ ID NO: 3) between helices B and C and a helix C (SEQ ID NO: 4) of IL-2 are similarly substituted with a loop x (SEQ ID NO: 10) and a helix c (SEQ ID NO: 11) of IL-15. Tryptophan (W) at position 115 in a helix D is further mutated into phenylalanine (F) which forms an aromatic ring interaction with the phenylalanine (F) at position 55 in the introduced helix b of IL-15 to stabilize a hydrophobic core, which in turn stabilizes a four-helix bundle structure, such that a newly-generated protein molecule IL-2/15 chimera does not bind to IL2Rα but can still bind to receptors β and γ.

Clinically, IL-2 at a low dose will preferentially bind to a high-affinity receptor with a chain a on a surface of Treg cells, which results in immunosuppression, such that a therapeutic effect cannot be achieved. IL-2 at a high dose can neutralize the immunosuppression caused by Treg activation by activating a large number of effector T cells, which will also cause many toxic side effects and AICD. Therefore, the technical solutions adopted by the present application can weaken or eliminate the binding to receptor α to reduce the IL-2-promoted anti-T cell proliferation activity and can also reduce the binding to endothelial cell receptor α to reduce or eliminate toxic side effects caused by IL-2 treatment. IL-15 does not have the functions of Treg activation and AICD (Waldmann T A et al, Nature Reviews Immunol 6: 595-601, 2006). In addition, because IL-15 is composed of different receptor subunits, IL-15 exhibits a more significant effect of promoting NK cell proliferation and maintaining memory T cells than IL-2. Therefore, based on the characteristics of IL-2 and IL-15, the present application blocks the binding to IL2Rα and retains the binding to IL2/15R β and γ.

In some embodiments, the IL-15 protein sequence introduced into IL-2 can bind to IL15Rα, and thus the IL15Rα (Sushi domain) can be co-expressed with an IL-2/15 chimera to obtain a heterodimer complex, which can stabilize the IL-2/15 chimera and improve the affinity for IL2/15Rβ to achieve superior biological activity. Further, Fc can undergo fusion expression at a C-terminus of the Sushi domain (such as SEQ ID NO: 15 or SEQ ID NO: 20) to achieve a long-acting purpose. Fc can be human IgG1 Fc, human IgG4 Fc, or mouse IgG2aa.1 Fc.

The present application will be further described below with reference to examples, and it should be understood that these examples are provided only for a purpose of illustration and are not intended to limit the protection scope of the present application.

The experimental methods which are not specified with specific conditions in the following examples are generally conducted under conventional conditions, such as conditions disclosed in *Molecular Cloning: Experiment Guide* (Sambrook et al., New York: Cold Spring Harbor Laboratory Press, 1989) or conditions recommended by manufacturers. Unless otherwise specified, the reagents used are commercially available or can be obtained through public channels.

Example 1 Preparation of IL-2/15 Chimeras from a Mammalian Cell

1.1 Synthesis and Construction of Expression Plasmids

GENEWIZ was entrusted to synthesize target gene fragments of the 4 proteins of an IL-2/15 chimera 1 (SEQ ID NO: 14), Sushi-hIgG1Fc (SEQ ID NO: 19), Sushi-hIgG4Fc (SEQ ID NO: 21), and Sushi-mIgG2aa.1Fc (SEQ ID NO: 22). Then the target gene fragments were each cloned to a position between EcoRI and HindIII sites of a pZD vector to obtain 4 expression plasmids, which were numbered as PM619, PM432, PM657, and PM599, respectively. On the basis of plasmid PM619, point mutation was conducted according to the method described in "*Molecular Cloning*", that is, phenylalanine (F) at position 115 (corresponding to position 121 of an amino acid sequence of a natural IL-2 molecule) was mutated into tryptophan (W) to obtain a plasmid of an IL-2/15 chimera 2 (SEQ ID NO: 23), which was numbered as PM824. Then the synthesized or constructed plasmids were each transformed into DH10B, sequenced, and preserved.

1.2 Plasmid Extraction and HEK293 Cell Preparation

1.2.1 Plasmid Extraction

According to the operation methods mentioned in "Qiagen Mini-prep Kit" and "Qiagen Endofree Maxi-prep Kit", the plasmids of the above two IL-2/15 chimeras and three types of Sushi-Fc were prepared.

1.2.2 HEK293 Cell Preparation

Freshly passaged HEK293 cells (National Research Council, Canada) at a density of $1\text{-}1.2\times10^6$/mL were used for transient expression.

1.3 Transient Expression in HEK293

1.3.1 Reagent Preparation

A) G418 solution: 250 mg of Geneticin™ was weighed and dissolved in 4.5 mL of ultrapure water (UPW). Then a resulting solution was diluted with UPW to 5 mL, filtered through a 0.22 μm filter membrane, and stored at −20° C.

B) PEI solution: 50 mg of PEI was weighed and dissolved in 45 mL of UPW. The pH was adjusted to 7.0 with 1 M NaOH. Then a resulting solution was diluted with UPW to 50 mL, filtered through a 0.22 μm filter membrane, and stored at −20° C.

C) Medium: 10 mL of 10% Pluronicd™ F-68 and 500 μL of G418 were added to 1 L of FreeStyle™ 293 Expression Medium.

D) A plasmid was added in advance to a 2 mL endotoxin-free centrifuge tube.

E) A suspension of freshly passaged cells at $1\text{-}1.2\times10^6$ cells/mL was prepared according to a volume required for transfection.

1.3.2 Preparation of a Transfection Reagent-Plasmid Complex

Solution A: plasmid 1 μg/mL+Opti-MEM™ 33.3 μL/mL
Solution B: PEI 2 μg/mL+Opti-MEM™ 33.3 μL/mL 1 mL of the solution B was poured into 1 mL of the solution A. The resulting mixture was thoroughly mixed and incubated for 10 min, and then the cell suspension was added.

The IL-2/15 chimera 1 was mixed with each of the three types of Sushi-Fc in a mass ratio of 1:1 (total amount: 1 μg/mL) for transfection. The IL-2/15 chimera 2 was mixed with the Sushi-hIgG4Fc in a mass ratio of 1:1 (total amount: 1 μg/mL) for transfection.

1.3.3 Medium Change

After cultivation for 4 h at 115 rpm, 36.8° C., and 5% $CO_2$, a culture was centrifuged at 800 g for 5 min. Then the FreeStyle™ 293 Expression Medium without Pluronicd™ F-68 and G418 was used instead.

1.3.4 Expression Cultivation and Harvest

After cultivation for 5 d at 115 rpm, 36.8° C., and 5% $CO_2$, a culture was centrifuged at 8,500 rpm for 15 min, and a culture supernatant was collected for purification.

1.4 Purification

Figure 1B:
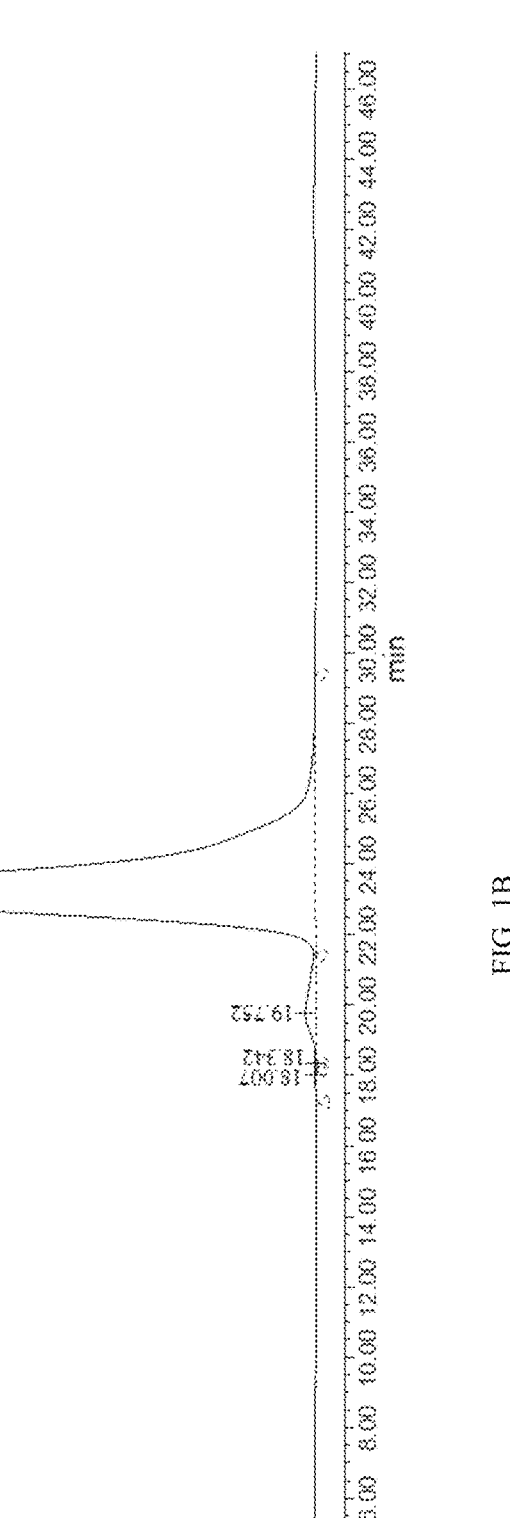
Figure 1C:
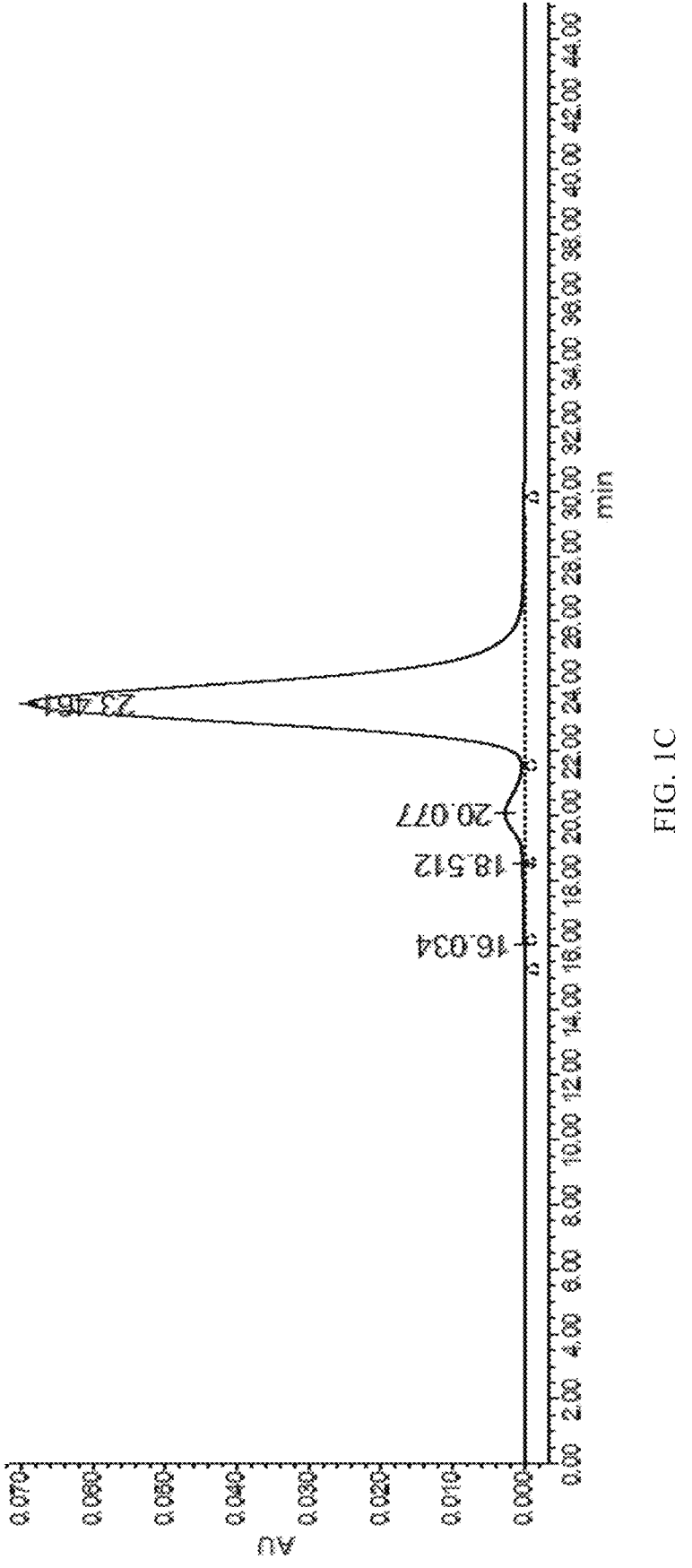
Figure 2:
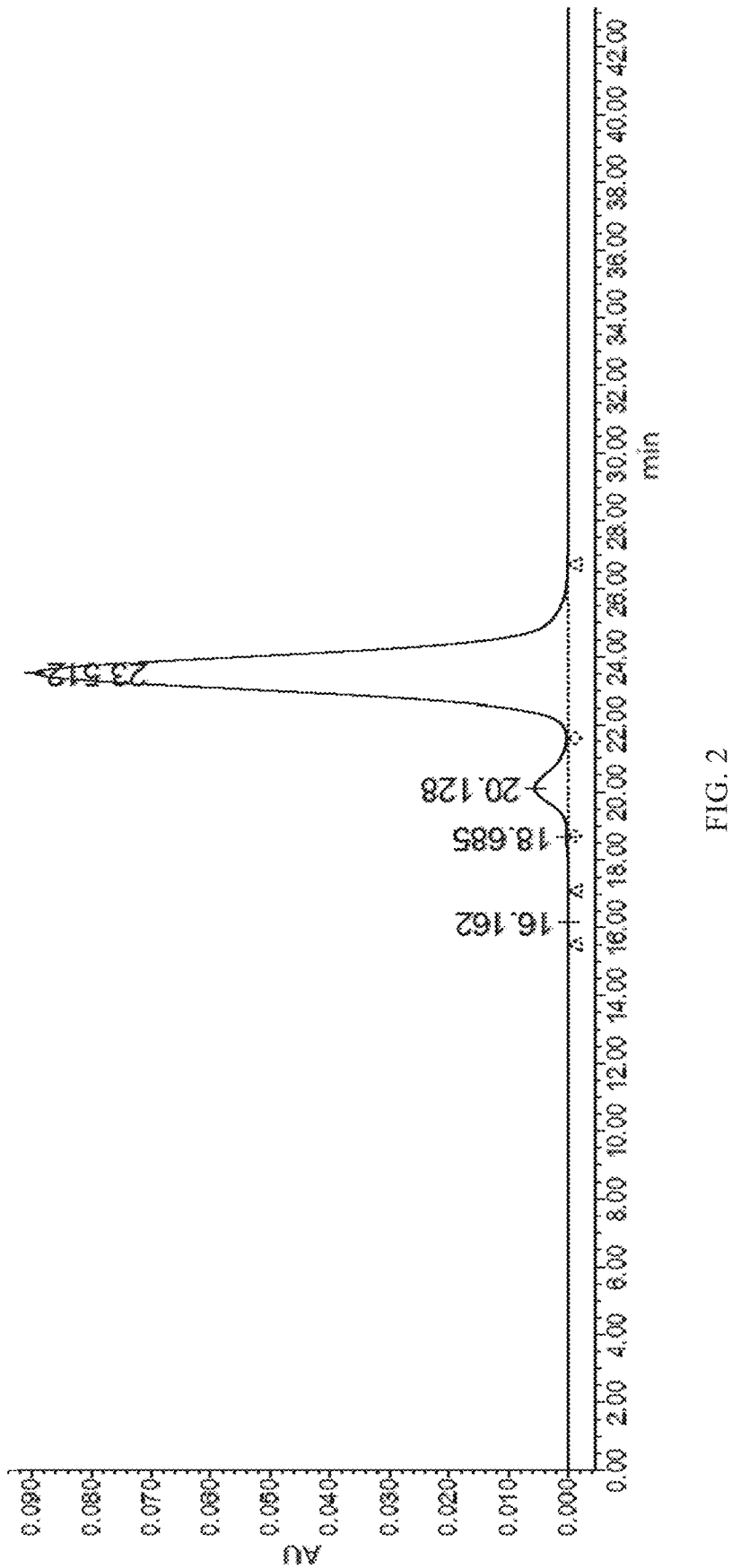
FIG. 2 shows an SEC-HPLC identification result of a purified heterodimer product of an IL-2/15 chimera 2 and a Sushi-hIgG4Fc protein in Example 1 of the present application.

The IL-2/15 chimera 1 was co-expressed with each of the Sushi-hIgG1Fc, Sushi-hIgG4Fc, and Sushi-mlgg2aa.1Fc, and heterodimer complexes could be generated during expression, which were respectively named as complex 1, complex 2, and complex 3 and all carried an Fc tag. Mabselect sure (Protein A, GE healthcare) was used for affinity purification, and a purification method was in accordance with instructions of a purification packing. Then further purification was conducted by gel filtration chromatography (GFC) (Superdex200 μg, GE Healthcare) to obtain a protein with high purity, and the aggregate was removed. The purity analysis was conducted using a high-performance liquid chromatography (HPLC) molecular sieve column (SEC-HPLC), and the results are shown in FIGS. 1A-1C. A main SEC peak of the purified protein was a single peak, indicating that the IL-2/15 chimera 1 was formed in a complex with each of the three types of Sushi-Fc, where the purity was high and the overall polymer and fragment content was less than 5%. The liquid chromatography-mass spectrometry analysis showed that the purified protein had two components, namely Sushi-Fc and IL-2/15, indicating that the protein expression and purification were successful. The IL-2/15 chimera 2 was also co-expressed with Sushi-hIgG4Fc to produce a complex, which was purified (as shown in FIG. 2).

Example 2 Preparation of an IL-2/15 Chimera from *Escherichia coli* (*E. coli*)

2.1 Synthesis and Construction of an Expression Plasmid

GENEWIZ was entrusted to synthesize a gene fragment (SEQ ID NO: 26) of an IL-2/15 chimera 1. Then the gene fragment was cloned to a position between NdeI and XhoI sites of a pET41a vector to obtain an expression plasmid, which was numbered as 1187.

2.2 Expression and Purification of the IL-2/15 Chimera in *E. coli*

According to the operation methods mentioned in "*Molecular Cloning*", the plasmid extraction and the transformation and expression of the plasmid in a strain BL21 (DE3) were conducted. The expression of the IL-2/15 chimera 1 was achieved according to a conventional prokaryotic expression method for proteins. Purification was conducted by classical denaturation and renaturation and chromatography techniques (for example, see: Yunier Rodriguez-Alvarez et al, Preparative Biochemistry and Biotechnology, 47: 9, 889-900) to obtain a pure chimeric protein.

Example 3 Determination of Binding Ability of IL-2/15 Chimeras to IL2Rα and IL2/15Rβ

BLI was used to determine the affinity of a target protein for a receptor by a method with reference to (Estep, P et al., High throughput solution Based measurement of antibody-antigen affinity and epitope binning. MAbs, 2013.5 (2): p. 270-8). The receptor proteins IL-15Rα-his, IL2Rα-his, and IL2/15Rβ-Fc/Fc used in the experiment were each produced by the company of the present application, and both an IL-2 derivative without IL2Rα binding and an IL-2 complex without IL2Rα binding were prepared according to the description in Patent Publication CN111018961A. An IL-15 (N72D)/Sushi-hIgG1Fc complex was prepared according to the literature (K.-p. Han et al./Cytokine 56 (2011) 804-810). A buffer was prepared according to the following formula: 10 mM HEPES, 150 mM NaCl, 3 mM EDTA, 0.1% BSA, and 0.05% tween20. Receptor proteins were each preimmobilized in advance on a corresponding sensor. Then the steps of baseline, loading, baseline, association, and dissociation were conducted according to the established method (see Estep, P et al., High throughput solution Based measurement of antibody-antigen affinity and epitope binning. MAbs, 2013. 5 (2): p. 270-8). Data acquisition and analysis were conducted using the Fortebio Octet RED96 software Data acquisition 11.0 and Data analysis 11.0, respectively. Results are shown in Table 1 (the smaller the value, the stronger the affinity). Compared with IL-2, the IL-2/15 chimera 1 and the IL-2/15 chimera 1-Sushi-Fc (complex 1, complex 2, or complex 3) did not bind to IL2Rα. The affinity of the IL-2/15 chimera 1 for IL-15Rα was less than 10 times lower than the affinity of IL-15 while the complex 1, complex 2, or complex 3 did not bind to IL-15Rα. The affinity of the IL-2/15 chimera 1 for IL2/15Rβ was significantly weaker than the affinity of the IL-15 and slightly weaker than the affinity of IL-2, while the affinity of the complex 1, complex 2, or complex 3 was stronger than the affinity of IL-2 or IL-15 but weaker than the affinity of the IL-15(N72D)/Sushi-hIgG1Fc complex.

TABLE 1

| Protein name | Affinity for IL2Rα (M) | Affinity for IL15Rα (M) | Affinity for IL2/15Rβ (M) |
|---|---|---|---|
| IL-2 | 8.21E-9 | N.B | 2.23E-7 |
| IL-15 | N.B | 2.08E-10 | 6.78E-8 |
| IL-2 derivative without IL2Rα binding | N.B | N.B | 2.8E-7 |
| IL-2 complex without IL2Rα binding | N.B | N.B | 1.95E-8 |
| Complex 1 | N.B | N.B | 3.37E-10 |
| Complex 2 | N.B | N.B | 6.54E-10 |
| Complex 3 | N.B | N.B | 5.12E-10 |
| IL-15(N72D)/Sushi-hIgG1Fc complex | N.B. | N.B | 5.56E-11 |
| IL-2/15 chimera 1 | N.B. | 3.89E-9 | 9.73E-7 |

Note:
N.B. represents no binding at 100 nM.

Example 4 Experiment on the Promotion of T Cell Proliferation

Figure 3:
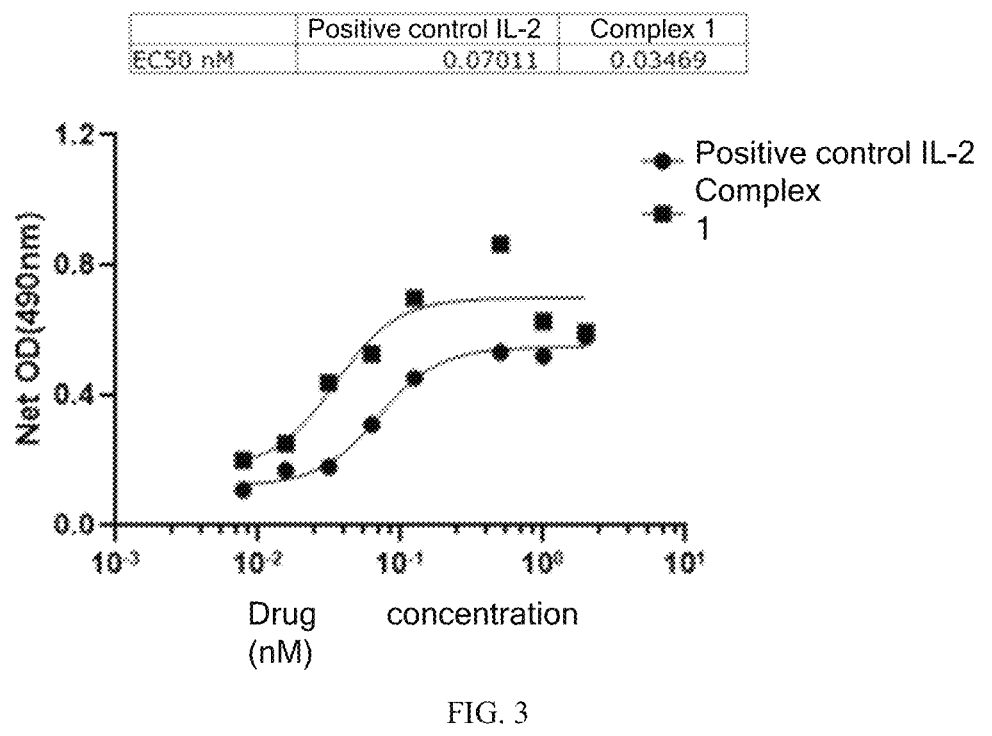

The proliferation experiment of CTLL-2 (T cell) is a common experiment to measure the activity of IL to stimulate immune cells at a cellular level. In this example, the biological activity of the IL-2/15 chimera 1 prepared in Example 1 was measured by the proliferation experiment of CTLL-2 cells. CTLL-2 cells (purchased from ATCC, Cat. No. ATCC® TIB-214™) was resuspended in a medium with FBS and Rat-T-Stim, and then inoculated into a 96-well plate at 21,000 cells/well. A positive control (IL-2) and a complex 1 to be tested were each serially diluted and added to the plate with an initial working concentration of 0.0078125 nM, and 3 replicate wells were set for each dilution concentration. A medium control well (100 μL of the cell+100 μL of the medium) was also set. The cells were incubated at 37° C. and 5% $CO_2$ for 72 h, then 20 μl of CellTiter96® AQueous One Solution Reagent (purchased from Promega, Cat #G3581) was added to each well, and then the plate was incubated at 37° C. and 5% $CO_2$ for 2 h to 4 h. A microplate reader was used to determine the absorbance (A) at a wavelength of 490 nm, and an $EC_{50}$ value was calculated. Results are shown in Table 2 and FIG. 3, and it can be seen that the complex 1 exhibited an obvious activity for promoting the proliferation of CTLL-2 (T cells), which was higher than an activity of the positive control IL-2.

TABLE 2

| | EC$_{50}$ value of each group | |
|---|---|---|
| | Positive control (IL-2) | Complex 1 |
| EC50 nM | 0.07011 | 0.03469 |

Example 5 Experiment on the Promotion of Mo7e Cell Proliferation

A Mo7e cell line (expressing IL-2/15R β and γ) was cultivated in a complete medium (RPMI1640+10% FBS+ GM-CSF (10 ng/mL)) at 37° C. and 5% $CO_2$. Cells in a logarithmic growth phase were harvested, then washed twice with PBS to remove cytokines, and then resuspended in a cytokine-free medium. A cell density was adjusted appropriately with the cytokine-free medium, and then a resulting cell suspension was added to a 96-well plate at 90 μL per well with 5,000 cells in total. The cells in the 96-well plate were cultivated at 37° C. and 5% $CO_2$ for later use. Serially diluted drug solutions were prepared with a final working concentration of 0.020116 μM, 9 concentrations, and 3.16-fold dilution. Then 10 μL of each of serially diluted samples was added to a corresponding experimental well in the 96-well plate with three replicate wells for each drug concentration. After the drug samples were added, cells in the 96-well plate were further cultivated at 37° C. and 5% $CO_2$ for 72 h and then analyzed by a Celltiter Glo assay kit (CTG, Promega). An equal volume of a CTG solution was added to each well. The cell plate was placed at room temperature for 20 min to stabilize a luminescence signal. A luminescence value was read, and data was collected. The data was analyzed using the GraphPad Prism 7.0 software and was fitted by a nonlinear S-curve regression to obtain a dose-response curve, and then an EC$_{50}$ value was calculated accordingly.

$$\text{Cell viability (\%)}=(\text{Lum}_{test\ dmg}-\text{Lum}_{medium\ control})/$$
$$(\text{Lum}_{solvent\ control}-\text{Lum}_{medium\ control})\times100\%.$$

In this experiment, hIgG1 and hIgG4 were used as controls, neither of which could promote cell proliferation. It can be seen from the results that the activity of the IL-2/15 chimera 1 alone was lower than the activity of IL-15 and higher than the activity of IL-2 and was about 10 times lower than the activity of IL-15. The complex of the IL-2/15 chimera 1 and Sushi exhibited a weaker activity than the IL-15(N72D)/Sushi-hIgG1Fc complex. Due to the drug toxicity caused by the high activity of IL-2/15Rβγ agonists clinically earlier, it is possible that the complex of the IL-2/15 chimera 1 and Sushi has superior safety.

TABLE 3

| Results of the experiment on the promotion of Mo7e cell proliferation | |
|---|---|
| Protein name | EC50 (nM) |
| IL-2 | 2.557 |
| IL-15 | 0.267 |
| Complex 2 | 0.329 |
| Complex 3 | 0.319 |
| IL-15(N72D)/Sushi-hIgG1Fc complex | 0.090 |
| IL-2/15 chimera 1 | 2.251 |
| hIgG1 control | N/A |
| hIgG4 control | N/A |

Example 6 Pre-Toxicological Test in Cynomolgus Monkeys

Cynomolgus monkeys were randomly divided into two groups, namely, a complex 2 group and an IL-15(N72D)/Sushi-hIgG1Fc complex group with one male and one female in each group. The monkeys were each intravenously injected with the drug at a dose of 1 mg/kg once a week, with twice in total. The clinical manifestations of the monkeys were observed, and the monkeys were weighed every day, and it was analyzed whether the drug was tolerated.

Figure 4:
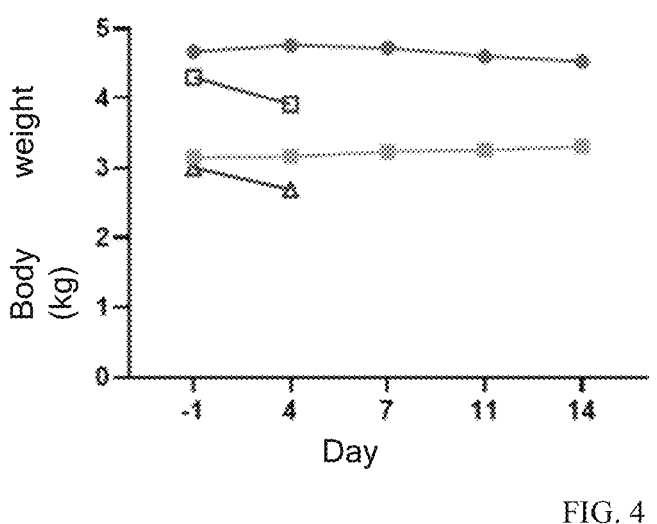
FIG. 4 shows pre-toxicological experiment results in Example 6 of the present application.

It was found from the test that, in the complex 2 group, the female monkey had a small amount of yellow loose stool on D2 to D4, but the body weights of both the male and the female were relatively stable for 14 d (as shown in FIG. 4), indicating that the dose of 1 mg/kg was tolerated. In the IL-15(N72D)/Sushi-hIgG1Fc complex group, both the male and the female showed lack of energy, decreased spontaneous activity, a small/medium amount of yellow loose stool, and sunken eye sockets on D3 to D4, and died on D4, indicating that the dose of 1 mg/kg was not tolerated.

Example 7 Pharmacodynamic Evaluation of an IL-2/15 Chimeric Complex in C57BL/6 Mouse Tumor Models Subcutaneously Transplanted with Mouse Cutaneous Melanoma B16F10

A B16F10 cell suspension at 5.0×10⁶ cells/mL was pipetted up and down for thorough mixing and then placed on ice. A right hindlimb of a mouse was subjected to hair removal and then disinfected with an iodophor cotton ball. Then 0.1 mL of the cell suspension was subcutaneously injected into the right hindlimb of the mouse with a 1 mL syringe at 5×10⁵ cells/point. On the day of inoculation with the tumor cells, mice were randomly divided into 3 groups according to their body weights with 5 mice in each group. The day when groups were made was regarded as experimental Day 0, and the administration was started on the second day (Day 1) after grouping. Administration and grouping information was shown in Table 4 below.

TABLE 4

| | | Grouping and administration information | | | | |
|---|---|---|---|---|---|---|
| Group | Number of animals | Compound treatment | Dose (mg/kg) | Administration volume (μL/g) | Administration route | Administration frequency |
| 1 | 5 | Vehicle (PBS) | — | 10 | i.v. | BIW Day 1, Day 4, Day 8, Day 11, Day 15, Day 18 |
| 2 | 5 | Complex 2 | 2 | 10 | i.v. | BIW Day 1, Day 4, Day 8, Day 11, Day 15, Day 18 |
| 3 | 5 | Complex 3 | 2 | 10 | i.v. | BIW Day 1, Day 4, Day 8, Day 11, Day 15, Day 18 |

After the tumor inoculation, the mice were routinely checked for tumor growth, mobility, diet, body weight, eyes, hair, and other abnormal behaviors, and a humane endpoint was given accordingly. After the grouping and administration, a tumor volume in a mouse was measured twice a week. A tumor volume was measured by a bi-directional measurement method. Major and minor diameters of a tumor were measured with a vernier caliper, and then a tumor volume was calculated using the formula $T=0.5 \times a \times b^2$, where a and b represent the major and minor diameters of the tumor, respectively.

A relative tumor growth inhibition (TGI) (%) was calculated according to the formula $TGI=1-T/C$ (%), where the T/C (%) represents a relative tumor proliferation rate, namely, a percentage of a relative tumor volume or weight of a treatment group to a relative tumor volume or weight of a control group at a specified time point; T and C represent relative tumor volumes (RTVs) of the treatment and control groups at a specific time point, respectively; and the T/C (%) was calculated as follows: $T/C$ (%)$=TRTV/CRTV\times100\%$ (TRTV: average RTV of the treatment group; CRTV: average RTV of the vehicle control group; and $RTV=V_t-V_0$, where $V_0$ represents a tumor volume of the animal at the time of grouping and $V_t$ represents a tumor volume of the animal after treatment).

Figure 5:
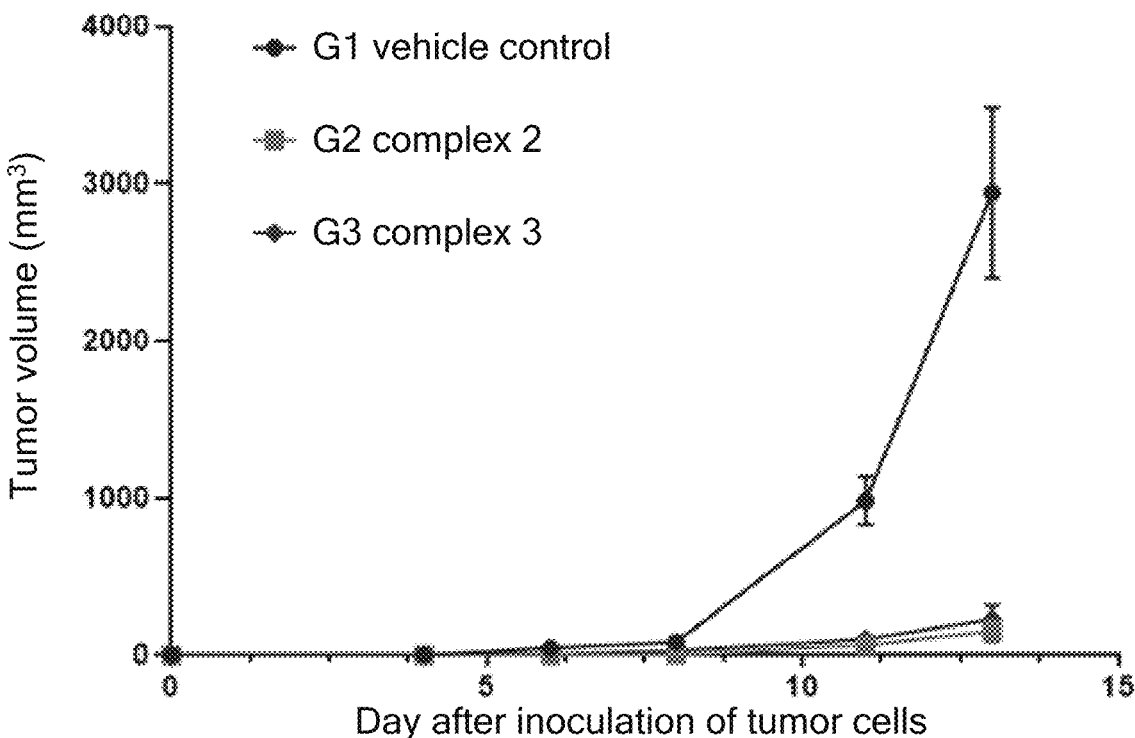
FIG. 5 shows antitumor effects of complexes for a representative cancer in Example 7 of the present application.

Results are shown in FIG. 5. In this experiment, the efficacy of the test drug when administered alone was verified in the C57BL/6 female mouse model subcutaneously inoculated with mouse melanoma B16F10 cells. In the G1 control group, on Day 13, an average tumor volume of the animals was $2942\pm545.3$ mm$^3$. In the G2 group administered with the complex 2 at 2 mg/kg BIW, on Day 13, the TGI (%) was 95%, which was significantly different from the control group ($p<0.01$). In the G3 group administered with the complex 3 at 2 mg/kg BIW, on Day 13, the TGI (%) was 92%, which was significantly different from the control group ($p<0.01$). The data showed that, during the 13-day administration experiment in the C57BL/6 mouse model inoculated with mouse melanoma tumor cells B16F10, the tested drug complex 2 or complex 3 exhibited strong efficacy with statistical difference ($p<0.01$) from the control group. There was no difference between the complex 2 and the complex 3, both of which exhibited a significant antitumor effect.

What is claimed is:

1. A protein heterodimer comprising a modified IL-2 comprising the amino acid sequence as shown in SEQ ID NO: 14 and a sushi domain of IL15 receptor (ILI5R) comprising the amino acid sequence as shown in SEQ ID NO: 19, SEQ ID NO: 21, or SEQ ID NO: 22.

2. A pharmaceutical composition comprising the protein heterodimer according to claim 1.

* * * * *

SEQUENCE LISTING

```
<160> NUMBER OF SEQ ID NOS: 26

<210> SEQ ID NO 1
<211> LENGTH: 24
<212> TYPE: PRT
<213> ORGANISM: Homo sapiens

<400> SEQUENCE: 1

Asn Asn Tyr Lys Asn Pro Lys Leu Thr Arg Met Leu Thr Phe Lys Phe
1               5                   10                  15

Tyr Met Pro Lys Lys Ala Thr Glu
            20

<210> SEQ ID NO 2
<211> LENGTH: 20
<212> TYPE: PRT
<213> ORGANISM: Homo sapiens

<400> SEQUENCE: 2

Leu Lys His Leu Gln Cys Leu Glu Glu Glu Leu Lys Pro Leu Glu Glu
1               5                   10                  15

Val Leu Asn Leu
            20

<210> SEQ ID NO 3
<211> LENGTH: 9
<212> TYPE: PRT
<213> ORGANISM: Homo sapiens

<400> SEQUENCE: 3

Ala Gln Ser Lys Asn Phe His Leu Arg
1               5

<210> SEQ ID NO 4
<211> LENGTH: 16
<212> TYPE: PRT
<213> ORGANISM: Homo sapiens

<400> SEQUENCE: 4

Pro Arg Asp Leu Ile Ser Asn Ile Asn Val Ile Val Leu Glu Leu Lys
1               5                   10                  15
```

-continued

```
<210> SEQ ID NO 5
<211> LENGTH: 16
<212> TYPE: PRT
<213> ORGANISM: Homo sapiens

<400> SEQUENCE: 5

Gly Ser Glu Thr Thr Phe Met Cys Glu Tyr Ala Asp Glu Thr Ala Thr
1               5                   10                  15

<210> SEQ ID NO 6
<211> LENGTH: 20
<212> TYPE: PRT
<213> ORGANISM: Homo sapiens

<400> SEQUENCE: 6

Ile Val Glu Phe Leu Asn Arg Trp Ile Thr Phe Cys Gln Ser Ile Ile
1               5                   10                  15

Ser Thr Leu Thr
            20

<210> SEQ ID NO 7
<211> LENGTH: 133
<212> TYPE: PRT
<213> ORGANISM: Homo sapiens

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 8
<211> LENGTH: 19
<212> TYPE: PRT
<213> ORGANISM: Homo sapiens

<400> SEQUENCE: 8

Gln Ser Met His Ile Asp Ala Thr Leu Tyr Thr Glu Ser Asp Val His
1               5                   10                  15

Pro Ser Cys

<210> SEQ ID NO 9
<211> LENGTH: 18
<212> TYPE: PRT
<213> ORGANISM: Homo sapiens
```

<400> SEQUENCE: 9

Lys Val Thr Ala Met Lys Cys Phe Leu Leu Glu Leu Gln Val Ile Ser
1               5                   10                  15

Leu Glu

<210> SEQ ID NO 10
<211> LENGTH: 5
<212> TYPE: PRT
<213> ORGANISM: Homo sapiens

<400> SEQUENCE: 10

Ser Gly Asp Ala Ser
1               5

<210> SEQ ID NO 11
<211> LENGTH: 16
<212> TYPE: PRT
<213> ORGANISM: Homo sapiens

<400> SEQUENCE: 11

Ile His Asp Thr Val Glu Asn Leu Ile Ile Leu Ala Asn Asn Ser Leu
1               5                   10                  15

<210> SEQ ID NO 12
<211> LENGTH: 21
<212> TYPE: PRT
<213> ORGANISM: Homo sapiens

<400> SEQUENCE: 12

Ser Ser Asn Gly Asn Val Thr Glu Ser Gly Cys Lys Glu Cys Glu Glu
1               5                   10                  15

Leu Glu Glu Lys Asn
            20

<210> SEQ ID NO 13
<211> LENGTH: 114
<212> TYPE: PRT
<213> ORGANISM: Homo sapiens

<400> SEQUENCE: 13

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Ala Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 14
<211> LENGTH: 127
<212> TYPE: PRT

-continued

```
<213> ORGANISM: Artificial Sequence
<220> FEATURE:
<223> OTHER INFORMATION: Amino acid sequence of IL-2/IL-15 chimera 1

<400> SEQUENCE: 14

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met His
            20                  25                  30

Ile Asp Ala Thr Leu Tyr Thr Glu Ser Asp Val His Pro Ser Cys Lys
        35                  40                  45

Val Thr Ala Met Lys Cys Phe Leu Leu Glu Leu Gln Val Ile Ser Leu
    50                  55                  60

Glu Ser Gly Asp Ala Ser Ile His Asp Thr Val Glu Asn Leu Ile Ile
65                  70                  75                  80

Leu Ala Asn Asn Ser Leu Ser Ser Asn Gly Asn Val Thr Glu Ser Gly
                85                  90                  95

Cys Lys Glu Cys Glu Glu Leu Glu Glu Lys Asn Ile Val Glu Phe Leu
            100                 105                 110

Asn Arg Phe Ile Thr Phe Ala Gln Ser Ile Ile Ser Thr Leu Thr
        115                 120                 125

<210> SEQ ID NO 15
<211> LENGTH: 65
<212> TYPE: PRT
<213> ORGANISM: Homo sapiens

<400> SEQUENCE: 15

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 16
<211> LENGTH: 175
<212> TYPE: PRT
<213> ORGANISM: Homo sapiens

<400> SEQUENCE: 16

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Ser Thr Val
65                  70                  75                  80

Thr Thr Ala Gly Val Thr Pro Gln Pro Glu Ser Leu Ser Pro Ser Gly
                85                  90                  95
```

```
Lys Glu Pro Ala Ala Ser Ser Pro Ser Ser Asn Asn Thr Ala Ala Thr
                100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175
```

<210> SEQ ID NO 17
<211> LENGTH: 219
<212> TYPE: PRT
<213> ORGANISM: Homo sapiens

<400> SEQUENCE: 17

```
Glu Leu Cys Asp Asp Asp Pro Pro Glu Ile Pro His Ala Thr Phe Lys
1                   5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
                180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln
        210                 215
```

<210> SEQ ID NO 18
<211> LENGTH: 232
<212> TYPE: PRT
<213> ORGANISM: Homo sapiens

<400> SEQUENCE: 18

```
Glu Pro Lys Ser Cys Asp Lys Thr His Thr Cys Pro Pro Cys Pro Ala
1                   5                   10                  15

Pro Glu Leu Leu Gly Gly Pro Ser Val Phe Leu Phe Pro Pro Lys Pro
                20                  25                  30
```

-continued

```
Lys Asp Thr Leu Met Ile Ser Arg Thr Pro Glu Val Thr Cys Val Val
        35              40              45

Val Asp Val Ser His Glu Asp Pro Glu Val Lys Phe Asn Trp Tyr Val
    50              55              60

Asp Gly Val Glu Val His Asn Ala Lys Thr Lys Pro Arg Glu Glu Gln
65              70              75              80

Tyr Asn Ser Thr Tyr Arg Val Val Ser Val Leu Thr Val Leu His Gln
                85              90              95

Asp Trp Leu Asn Gly Lys Glu Tyr Lys Cys Lys Val Ser Asn Lys Ala
            100             105             110

Leu Pro Ala Pro Ile Glu Lys Thr Ile Ser Lys Ala Lys Gly Gln Pro
            115             120             125

Arg Glu Pro Gln Val Tyr Thr Leu Pro Pro Ser Arg Asp Glu Leu Thr
    130             135             140

Lys Asn Gln Val Ser Leu Thr Cys Leu Val Lys Gly Phe Tyr Pro Ser
145             150             155             160

Asp Ile Ala Val Glu Trp Glu Ser Asn Gly Gln Pro Glu Asn Asn Tyr
            165             170             175

Lys Thr Thr Pro Pro Val Leu Asp Ser Asp Gly Ser Phe Phe Leu Tyr
            180             185             190

Ser Lys Leu Thr Val Asp Lys Ser Arg Trp Gln Gln Gly Asn Val Phe
        195             200             205

Ser Cys Ser Val Met His Glu Ala Leu His Asn His Tyr Thr Gln Lys
        210             215             220

Ser Leu Ser Leu Ser Pro Gly Lys
225             230
```

<210> SEQ ID NO 19
<211> LENGTH: 297
<212> TYPE: PRT
<213> ORGANISM: Artificial Sequence
<220> FEATURE:
<223> OTHER INFORMATION: Amino acid sequence of Sushi-hIgG1Fc

<400> SEQUENCE: 19

```
Ile Thr Cys Pro Pro Pro Met Ser Val Glu His Ala Asp Ile Trp Val
1               5               10              15

Lys Ser Tyr Ser Leu Tyr Ser Arg Glu Arg Tyr Ile Cys Asn Ser Gly
            20              25              30

Phe Lys Arg Lys Ala Gly Thr Ser Ser Leu Thr Glu Cys Val Leu Asn
        35              40              45

Lys Ala Thr Asn Val Ala His Trp Thr Thr Pro Ser Leu Lys Cys Ile
    50              55              60

Arg Glu Pro Lys Ser Cys Asp Lys Thr His Thr Cys Pro Pro Cys Pro
65              70              75              80

Ala Pro Glu Leu Leu Gly Gly Pro Ser Val Phe Leu Phe Pro Pro Lys
            85              90              95

Pro Lys Asp Thr Leu Met Ile Ser Arg Thr Pro Glu Val Thr Cys Val
            100             105             110

Val Val Asp Val Ser His Glu Asp Pro Glu Val Lys Phe Asn Trp Tyr
        115             120             125

Val Asp Gly Val Glu Val His Asn Ala Lys Thr Lys Pro Arg Glu Glu
        130             135             140

Gln Tyr Asn Ser Thr Tyr Arg Val Val Ser Val Leu Thr Val Leu His
145             150             155             160
```

-continued

```
Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295
```

```
<210> SEQ ID NO 20
<211> LENGTH: 78
<212> TYPE: PRT
<213> ORGANISM: Homo sapiens

<400> SEQUENCE: 20
```

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Ser
65                  70                  75
```

```
<210> SEQ ID NO 21
<211> LENGTH: 293
<212> TYPE: PRT
<213> ORGANISM: Artificial Sequence
<220> FEATURE:
<223> OTHER INFORMATION: Amino acid sequence of Sushi-hIgG4Fc

<400> SEQUENCE: 21
```

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Ser Lys Tyr Gly Pro Pro Cys Pro Pro Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
```

-continued

```
                100              105              110

Val Ser Gln Glu Asp Pro Glu Val Gln Phe Asn Trp Tyr Val Asp Gly
        115              120              125

Val Glu Val His Asn Ala Lys Thr Lys Pro Arg Glu Glu Gln Phe Asn
    130              135              140

Ser Thr Tyr Arg Val Val Ser Val Leu Thr Val Leu His Gln Asp Trp
145              150              155              160

Leu Asn Gly Lys Glu Tyr Lys Cys Lys Val Ser Asn Lys Gly Leu Pro
            165              170              175

Ser Ser Ile Glu Lys Thr Ile Ser Lys Ala Lys Gly Gln Pro Arg Glu
            180              185              190

Pro Gln Val Tyr Thr Leu Pro Pro Ser Gln Glu Glu Met Thr Lys Asn
        195              200              205

Gln Val Ser Leu Thr Cys Leu Val Lys Gly Phe Tyr Pro Ser Asp Ile
    210              215              220

Ala Val Glu Trp Glu Ser Asn Gly Gln Pro Glu Asn Asn Tyr Lys Thr
225              230              235              240

Thr Pro Pro Val Leu Asp Ser Asp Gly Ser Phe Phe Leu Tyr Ser Arg
            245              250              255

Leu Thr Val Asp Lys Ser Arg Trp Gln Glu Gly Asn Val Phe Ser Cys
            260              265              270

Ser Val Met His Glu Ala Leu His Asn His Tyr Thr Gln Lys Ser Leu
        275              280              285

Ser Leu Ser Leu Gly
    290
```

```
<210> SEQ ID NO 22
<211> LENGTH: 298
<212> TYPE: PRT
<213> ORGANISM: Artificial Sequence
<220> FEATURE:
<223> OTHER INFORMATION: Amino acid sequence of Sushi-mIgG2aa.1Fc

<400> SEQUENCE: 22

Ile Thr Cys Pro Pro Pro Met Ser Val Glu His Ala Asp Ile Trp Val
1               5               10              15

Lys Ser Tyr Ser Leu Tyr Ser Arg Glu Arg Tyr Ile Cys Asn Ser Gly
            20              25              30

Phe Lys Arg Lys Ala Gly Thr Ser Ser Leu Thr Glu Cys Val Leu Asn
        35              40              45

Lys Ala Thr Asn Val Ala His Trp Thr Thr Pro Ser Leu Lys Cys Ile
    50              55              60

Arg Glu Pro Arg Gly Pro Thr Ile Lys Pro Cys Pro Pro Cys Lys Cys
65              70              75              80

Pro Ala Pro Asn Ala Glu Gly Ala Pro Ser Val Phe Ile Phe Pro Pro
            85              90              95

Lys Ile Lys Asp Val Leu Met Ile Ser Leu Ser Pro Ile Val Thr Cys
            100              105              110

Val Val Val Asp Val Ser Glu Asp Asp Pro Asp Val Gln Ile Ser Trp
        115              120              125

Phe Val Asn Asn Val Glu Val His Thr Ala Gln Thr Gln Thr His Arg
    130              135              140

Glu Asp Tyr Asn Ser Thr Leu Arg Val Val Ser Ala Leu Pro Ile Gln
145              150              155              160

His Gln Asp Trp Met Ser Gly Lys Glu Phe Lys Cys Lys Val Asn Asn
```

-continued

```
                165                 170                 175

Lys Gln Leu Pro Ser Ser Ile Glu Arg Thr Ile Ser Lys Pro Lys Gly
                180                 185                 190

Ser Val Arg Ala Pro Gln Val Tyr Val Leu Pro Pro Glu Glu Glu
                195                 200                 205

Met Thr Lys Lys Gln Val Thr Leu Thr Cys Met Val Thr Asp Phe Met
            210                 215                 220

Pro Glu Asp Ile Tyr Val Glu Trp Thr Asn Asn Gly Lys Thr Glu Leu
        225                 230                 235                 240

Asn Tyr Lys Asn Thr Glu Pro Val Leu Asp Ser Asp Gly Ser Tyr Phe
                245                 250                 255

Met Tyr Ser Lys Leu Arg Val Glu Lys Lys Asn Trp Val Glu Arg Asn
                260                 265                 270

Ser Tyr Ser Cys Ser Val Val His Glu Gly Leu His Asn His His Thr
                275                 280                 285

Thr Lys Ser Phe Ser Arg Thr Pro Gly Lys
        290                 295
```

<210> SEQ ID NO 23
<211> LENGTH: 127
<212> TYPE: PRT
<213> ORGANISM: Artificial Sequence
<220> FEATURE:
<223> OTHER INFORMATION: Amino acid sequence of IL-2/15 chimera 2

<400> SEQUENCE: 23

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met His
                20                  25                  30

Ile Asp Ala Thr Leu Tyr Thr Glu Ser Asp Val His Pro Ser Cys Lys
            35                  40                  45

Val Thr Ala Met Lys Cys Phe Leu Leu Glu Leu Gln Val Ile Ser Leu
        50                  55                  60

Glu Ser Gly Asp Ala Ser Ile His Asp Thr Val Glu Asn Leu Ile Ile
65                  70                  75                  80

Leu Ala Asn Asn Ser Leu Ser Ser Asn Gly Asn Val Thr Glu Ser Gly
                85                  90                  95

Cys Lys Glu Cys Glu Glu Leu Glu Glu Lys Asn Ile Val Glu Phe Leu
                100                 105                 110

Asn Arg Trp Ile Thr Phe Ala Gln Ser Ile Ile Ser Thr Leu Thr
            115                 120                 125
```

<210> SEQ ID NO 24
<211> LENGTH: 228
<212> TYPE: PRT
<213> ORGANISM: Homo sapiens

<400> SEQUENCE: 24

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60
```

-continued

```
Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly
225

<210> SEQ ID NO 25
<211> LENGTH: 233
<212> TYPE: PRT
<213> ORGANISM: Homo sapiens

<400> SEQUENCE: 25

Glu Pro Arg Gly Pro Thr Ile Lys Pro Cys Pro Pro Cys Lys Cys Pro
1               5                   10                  15

Ala Pro Asn Ala Glu Gly Ala Pro Ser Val Phe Ile Phe Pro Pro Lys
            20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
        50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Gln Leu Pro Ser Ser Ile Glu Arg Thr Ile Ser Lys Pro Lys Gly Ser
            115                 120                 125
```

```
Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

```
<210> SEQ ID NO 26
<211> LENGTH: 381
<212> TYPE: DNA
<213> ORGANISM: Artificial Sequence
<220> FEATURE:
<223> OTHER INFORMATION: Amino acid sequence of synthesized IL-2/15
      chimera 1

<400> SEQUENCE: 26
gcgccgacga gcagtagcac caaaaaaacg cagctgcagc tggaacatct gttactggat       60
ctgcagatga ttctgaacgg cattcagagc atgcatattg atgcgaccct gtataccgaa      120
agcgatgtgc atccgagctg caaagtgacc gcgatgaaat gctttctgct ggaactgcaa      180
gtgattagcc tggaaagcgg cgatgcgagc attcatgata ccgtggaaaa cctgattatt      240
ctggcgaaca acagcctgag cagcaacggc aacgtgaccg aaagcggctg caaagaatgc      300
gaagaactgg aagaaaaaaa cattgtggaa tttctgaacc gctttattac ctttgcgcag      360
agcattatta gcaccctgac c                                              381
```